United States Patent
Miller et al.

(10) Patent No.: US 12,059,670 B2
(45) Date of Patent: Aug. 13, 2024

(54) NICKEL ALLOY CATALYSTS FOR LIGHT ALKANE DEHYDROGENATION

(71) Applicant: PURDUE RESEARCH FOUNDATION, West Lafayette, IN (US)

(72) Inventors: Jeffrey T. Miller, West Lafayette, IN (US); Guanghui Zhang, West Lafayette, IN (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 447 days.

(21) Appl. No.: 16/635,603

(22) PCT Filed: Jul. 31, 2018

(86) PCT No.: PCT/US2018/044597
§ 371 (c)(1),
(2) Date: Jan. 31, 2020

(87) PCT Pub. No.: WO2019/028018
PCT Pub. Date: Feb. 7, 2019

(65) Prior Publication Data
US 2020/0238259 A1 Jul. 30, 2020

Related U.S. Application Data

(60) Provisional application No. 62/539,680, filed on Aug. 1, 2017.

(51) Int. Cl.
*B01J 23/883* (2006.01)
*B01J 23/825* (2006.01)
(Continued)

(52) U.S. Cl.
CPC ........... *B01J 23/883* (2013.01); *B01J 23/825* (2013.01); *B01J 37/0205* (2013.01); *B01J 37/08* (2013.01);
(Continued)

(58) Field of Classification Search
None
See application file for complete search history.

(56) References Cited

U.S. PATENT DOCUMENTS 6,258,992 B1   7/2001   Karim et al.
2002/0055664 A1   5/2002   Liu

FOREIGN PATENT DOCUMENTS

EP   0568303   11/1993

OTHER PUBLICATIONS

Siahvashi et al., Nonoxidative and oxidative propane dehydrogenation over bimetallic Mo—Ni/Al2O3 catalyst, Ind. Eng. Chem. Res., 2013, 52, 4017-4026 (Year: 2013).*

(Continued)

*Primary Examiner* — Sheng H Davis
*Assistant Examiner* — Keling Zhang
(74) *Attorney, Agent, or Firm* — Edmonds & Cmaidalka, P.C.

(57) ABSTRACT

A novel catalyst composition and its use in the dehydrogenation of alkanes to olefins. The catalyst comprises a Group VIII noble metal selected from the group consisting of nickel, iron, cobalt, and combinations thereof, and a metal selected from the group consisting of molybdenum, indium, phosphorous, zinc, and combinations thereof, on a support. The catalyst composition is an active and selective catalyst for the catalytic dehydrogenation of alkanes to olefins.

12 Claims, 7 Drawing Sheets

Propane dehydrogenation product selectivity of Ni/C catalyst (51) Int. Cl.
  *B01J 37/02*   (2006.01)
  *B01J 37/08*   (2006.01)
  *B01J 37/16*   (2006.01)
  *C07C 5/48*    (2006.01)

(52) U.S. Cl.
  CPC ............... *B01J 37/16* (2013.01); *C07C 5/48* (2013.01); *C07C 2523/825* (2013.01); *C07C 2523/883* (2013.01)

(56) References Cited

OTHER PUBLICATIONS https://www.angelo.edu/faculty/kboudrea/periodic/trans_transition.htm (Year: 2015).*

Tan et al., Propane dehydrogenation over alumina-supported iron/phosphorus catalysts: structure evolution of iron species leading to high activity and propylene selectivity, ACS Catal., 2016, 6, 5673-5683 (Tan) (Year: 2016).*

Bagheri et al., Titanium dioxide as a catalyst support in heterogeneous catalysis, The Scientific World Journal, 2014, 727496 (Bagheri) (Year: 2014).*

International Search Report and Written Opinion for International Application No. PCT/US2018/044597 mailed on Oct. 1, 2018.

Shu, Y. et al.; The effect of impregnation sequence on the hydrogenation activity and selectivity of supported Pt/Ni bimetallic catalysts; Applied Catalysis A: General; May 1, 2008; vol. 339, No. 2; p. 170.

* cited by examiner

Fig. 1

Propane dehydrogenation product selectivity of Ni/C catalyst

Fig. 2

Propane dehydrogenation product selectivity of Ni-Mo/C catalyst

Fig. 3

Propane dehydrogenation results of Ni/SiO$_2$ catalyst

Propane dehydrogenation results of Ni-In/SiO$_2$

Fig. 5

XANES and EXAFS spectra of Ni nanoparticles and Ni-In/SiO$_2$ after reduction at 550 °C 5(a)      5(b)

Fig. 6

XRD pattern of Ni-In/SiO$_2$ after reduction at 550 °C

Fig. 7

XANES and EXAFS spectra of Ni-Ga/SiO$_2$, Ni NPs and NiO

XRD pattern of Ni-Ga/SiO$_2$

8(a)  8(b)

Dehydrogenation results of Ni-Ga/SiO$_2$ at 550 °C
(Reaction conditions: 0.5 g of Ni-Ga/SiO$_2$, 50 mL/min 5% C$_3$H$_8$/N$_2$)

Dehydrogenation results of (a) Ni-Sb/SiO$_2$ catalyst and (b) Ni-Bi/SiO$_2$ catalyst 11 (a)

11 (b)

NICKEL ALLOY CATALYSTS FOR LIGHT ALKANE DEHYDROGENATION

BACKGROUND

The present disclosure is directed to new catalyst compositions for the dehydrogenation of light alkanes, especially gaseous alkanes, e.g., ethane, propane, butanes and pentanes, to their respective alkene derivatives. The alkenes, commonly known as olefins, have a high value as precursors to fuels, chemicals, and polymers such as polyethylene and polypropylene.

More efficient utilization of petroleum and gas reserves is an important strategy for the deployment of future energy generation. Shale gas has become an increasingly important source of natural gas in the United States, and the U.S. government's Energy Information Administration predicts that by 2040, approximately 70 percent of the United States' natural gas supply will come from shale gas. The transformation of shale gas to transportation fuels, fine chemicals and polymers is one of the strategies to utilize the shale gas reserves to their highest value.

Current state-of-the-art olefin production includes thermal cracking of alkanes at high temperatures. For hydrocarbons with three or more carbons, thermal cracking results in mixtures of C—C and C—H cracked products, resulting in a mix of products that include propylene, ethylene, hydrogen, and methane. The resulting products must then be separated cryogenically at great cost.

Another known method for olefin production includes catalytic dehydrogenation (of propane) by metallic Pt or Cr oxide supported catalysts. Light alkane dehydrogenation is a reaction through which light alkanes are converted into light olefins and hydrogen. Thermodynamically, it is highly endothermic and equilibrium-limited. Due to equilibrium limitations, these selective alkane dehydrogenation reactions are typically carried out at a high, but narrow temperature range to maximize the olefin yield and minimize yields of undesired products such as alkynes, diolefins, and cracking products (lower molecular weight alkane olefin mixtures). A temperature typically above 500° C. is needed for the reaction to achieve theoretical conversion of 50% under a pressure of from 0.2 to 3 bar. At this temperature range, side reaction hydrogenolysis, which results in methane and coke formation can occur and lead to fast catalyst deactivation if conventional noble metal catalysts are used. Selective conversion of $C_3$ or higher hydrocarbons is critical to advancing the art of alkane dehydrogenation. There is a need for improved catalyst compositions for the dehydrogenation reactions of alkanes to alkenes.

BRIEF DESCRIPTION OF THE DRAWINGS

The accompanying drawings are incorporated into and form a part of the specification to illustrate aspects and examples of the present disclosure. These figures together with the description serve to explain the general principles of the disclosure. The figures are only for the purpose of illustrating examples of how the various aspects of the disclosure can be made and used and are not to be construed as limiting the disclosure to only the illustrated and described examples.

DETAILED DESCRIPTION

The following detailed description illustrates embodiments of the present disclosure. These embodiments are described in sufficient detail to enable a person of ordinary skill in the art to practice these embodiments without undue experimentation. It should be understood, however, that the embodiments and examples described herein are given by way of illustration only, and not by way of limitation. Various substitutions, modifications, additions, and rearrangements may be made that remain potential applications of the disclosed techniques. Therefore, the description that follows is not to be taken as limiting on the scope of the appended claims. In particular, an element associated with a particular embodiment should not be limited to association with that particular embodiment but should be assumed to be capable of association with any embodiment discussed herein.

Definitions

For the purpose of this description and appended claims, the following terms are defined.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All processes described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

The term "alkane" means substantially saturated compounds containing hydrogen and carbon only, e.g., those containing ≤1% (molar basis) of unsaturated carbon atoms. The term alkane encompasses $C_1$ to $C_6$ linear, iso, and cyclo alkanes.

As used herein, an "alkene" or "olefin" refers to any unsaturated hydrocarbon containing one or more pairs of carbon atoms linked by a double bond. The olefins described herein include cyclic or aliphatic olefins, and include mono-olefins, di-olefins, tri-olefins, etc.

As used herein, a "bimetallic catalyst" is a catalyst having at least two metal components. The term does not limit the number of metal components to only two. The two metals are, at least partially present in the metallic phase and/or in a metallic alloy state.

The term "$C_n$" hydrocarbon wherein n is a positive integer, e.g., 1, 2, 3, 4, or 5, means hydrocarbon having n carbon atom(s) per molecule. The term "$C_{n+}$" hydrocarbon wherein n is a positive integer, e.g., 1, 2, 3, 4, or 5, means hydrocarbon having at least n carbon atom(s) per molecule. The term "$C_{n-}$" hydrocarbon wherein n is a positive integer, e.g., 1, 2, 3, 4, or 5, means hydrocarbon having no more than n number of carbon atom(s) per molecule.

As used herein, a "catalyst" is any substance or material which changes the rate of conversion of alkanes to alkenes but is not, itself, consumed.

The term "hydrocarbon" means compounds containing hydrogen bound to carbon, and encompasses (i) saturated hydrocarbon, (ii) unsaturated hydrocarbon, and (iii) mixtures of hydrocarbons, including mixtures of hydrocarbons (saturated and/or unsaturated) having different values of n.

The present disclosure relates generally to dehydrogenation reactions of alkanes to olefins. More particularly, the present disclosure relates to catalysts which can enable dehydrogenation reactions of alkanes to olefins. Embodiments of the present disclosure provide a method to produce such catalysts. The catalytic dehydrogenation of hydrocarbons according to the formula $C_nH_{2n+2} \leftrightarrow C_nH_{2n}+H_2$, is a highly endothermic equilibrium reaction, the reaction rate of which is limited thermodynamically and which depends on the respective partial pressures and temperature. The dehydrogenation reaction is favored by low partial pressures of the hydrocarbons and by high temperatures.

The present disclosure is directed to novel catalyst compositions and their respective use in the dehydrogenation of alkanes to olefins. The catalyst is bimetallic and comprises a combination of nickel, cobalt, iron and a metal selected from the group consisting of molybdenum, indium phosphorous, zinc, and combinations thereof, on a support. The catalyst is an active and selective catalyst for the catalytic dehydrogenation of alkanes to olefins while retaining high activity and selectivity even following repeated regeneration by calcination in oxygen and reduction in hydrogen.

Commercially available light alkane dehydrogenation catalysts currently in use are Pt—Sn and CrOx based catalysts supported on an alkali (Na/K) modified alumina. A Pt—Sn catalyst is used in the Oleflex process which utilizes a continuous fluidized catalyst bed. The Oleflex process is commercially offered by Honeywell UOP. Alternately a CrOx catalyst is used in the Catofin process licensed by Lummus Technology, a CB&I company, which uses parallel fixed beds. Both of these catalysts are reported to achieve selectivity above 90%. Nevertheless, frequent regeneration is needed in industrial operation and the catalysts have a total life of approximately 1 to 3 years.

Zinc has also been investigated widely and applied in industry. Previous patents have reported few other promoters that are IIIA and IVA elements (mainly Ga and In). Addition of Ga is claimed to improve the selectivity and stability of a Pt catalyst. In a $Pt(ZnO/Ga_2O_3)$—$SiO_2$ catalyst reported in U.S. Pat. No. 5,346,871, PtZn and PtGa alloys are formed in-situ in isobutene dehydrogenation, which is related to the high selectivity and long catalyst life.

Due to equilibrium limitations, these selective alkane dehydrogenation reactions are typically carried out at a high, but narrow temperature range to maximize the alkene yield and minimize yields of undesired products such as alkynes, diolefins, and cracking products (lower molecular weight alkane olefin mixtures). Useful catalysts must exhibit high activity and selectivity for the desired dehydrogenation process and a minimal rate of deactivation. Dehydrogenation reactions are known to produce coke, which is highly refractory and the coke formation leads to catalyst deactivation. Coke removal can require combustion in oxygen containing gas at temperatures greater than 600° C. Desirable catalysts, therefore, must retain high alkane dehydrogenation activity following high temperature regeneration.

Nickel (Ni) is the fourth most abundant transitional metal on earth. It is of low cost compared with Pt group metals, and of lower toxicity compared with the Cr catalysts industrially used for propane dehydrogenation. Ni has been extensively used in reforming and selective hydrogenation reactions. However, due to its high coke deposition and low selectivity toward olefin products, Ni has not been used in high-temperature dehydrogenation of small alkanes. The present disclosure includes new Ni catalysts for alkane dehydrogenation at high temperature that yield high stability and olefin selectivity. The new Ni catalysts are reproducible and robust for the conversion of small alkanes to olefins. The elements Co and Fe have similar metallic properties as nickel and should form similar alloys with similar chemical properties.

The catalysts of the present disclosure can be prepared by impregnating a support material with a Group VIII noble metal selected from the group consisting of nickel, iron, cobalt, and combinations thereof, to form a precursor. The precursor can then be dried and calcined. In an embodiment the Group VIII noble metal is nickel. In an embodiment the Group VIII noble metal is present in an amount ranging from 0.001 wt % to 30 wt %, optionally 0.001 wt %, to about 20 wt %, optionally 0.001 wt % to about 10 wt %, optionally from about 0.01 wt % to about 10 wt %, optionally from about 0.1 wt % to about 5 wt %, optionally from about 1.0 wt % to about 5 wt %, calculated on an elemental basis of the final catalyst composition on an elemental basis of the dehydrogenation catalyst composition.

The catalysts of the present disclosure can be prepared by impregnating a support material with molybdenum, indium, phosphorous, zinc or combinations thereof, to form a precursor. The precursor can then be dried and calcined. The amount of molybdenum, indium, phosphorous, zinc or combinations thereof, to be impregnated can range from about 0.001 wt % to about 30 wt %, optionally 0.001 wt %, to about 20 wt %, optionally 0.001 wt % to about 10 wt %, optionally from about 0.01 wt % to about 10 wt %, optionally from about 0.1 wt % to about 5 wt %, optionally from about 1.0 wt % to about 5 wt %, calculated on an elemental basis of the final catalyst composition.

The impregnations can be accomplished via the incipient wetness technique; however, other suitable techniques known to those skilled in the art are also suitable. An absorption technique from a dilute or concentrated solution, with subsequent filtration or evaporation to effect uptake of the metallic component, may also be used. Frequently, the pH of the solution will be adjusted to provide for optimum intercalation. In an embodiment the pH can be limited to between 8-14, optionally between 9-13, optionally between 10-12, optionally between 10.5-11.5, optionally the pH can be held at 11 throughout the impregnation procedure. Contacting time can be anywhere from at least about 1 minute to about 1 week, optionally about 1 minute to 1 day, optionally, about 1 to about 1 hour. In some instances, the higher the contacting temperature the shorter the contacting time that is necessary. Such contacting times can be readily determinable by one skilled in the art. The resulting material can then be separated by any conventional means, washed and dried. The impregnated support can then be dried followed by calcination and reduction.

The drying can be conducted at ambient temperature at first, such as for about 3 hours, followed by an elevated temperature, such as about 125° C. for about 8 hours. The calcination can be conducted at increasingly elevated temperature, such as at a temperature from 200° C. to 650° C., in the presence of oxygen, or in an air stream, or in the presence of a mixture of oxygen and an inert gas. In an example, the calcination can be about 200° C. for 30 minutes, and then 550° C. for 30 minutes or longer. The calcination process can be a staged calcination, wherein the temperatures are changed throughout the process. The temperature changes need not be a linear increase, but can be increased for example from 200° C. to 400° C. and held at 400° C. followed by another increase, etc. However, linear increases in temperature can also be used. This calcination can be conducted for periods ranging from about 30 minutes to 24 hours in either flowing or static gases. After calcination, the catalyst can be reduced in flowing hydrogen, or a hydrogen containing inert gas stream, at increasingly elevated temperatures, such as at 200° C. for 30 minutes and then at 550° C. for 30 minutes. The times, temperatures and rates of change during the drying, calcination and reducing process of the impregnated support are variable, can be readily determinable by one skilled in the art, and is not to be a limitation upon the present disclosure.

The metals can be added in any suitable manner known in the art, such as non-limiting examples of supported on a substrate or an inert support, added to a binder, placed on or within a zeolite or other catalyst support, such as by ion exchange, incipient wetness impregnation, pore volume impregnation, soaking, percolation, wash coat, precipitation, and gel formation.

The various elements that make up the components for the catalyst can be derived from any suitable source, such as in their elemental form, or in compounds or coordination complexes of an organic or inorganic nature, such as carbonates, oxides, hydroxides, nitrates, acetates, chlorides, phosphates, sulfides and sulfonates. The elements and/or compounds can be prepared by any suitable method known in the art for the preparation of such materials.

The term "support" or "substrate" as used herein is not meant to indicate that this component is necessarily inactive, while the other metals and/or promoters are the active species. On the contrary, the support or substrate can be an active part of the catalyst. The term substrate would merely imply that the substrate makes up a significant quantity, generally 10% or more by weight, of the entire catalyst. The active metals individually can range from 0.001% to 30% by weight of the catalyst, optionally from 0.001% to 25%, optionally from 0.001% to 20%, optionally from 0.001% to 15%, optionally from 0.001% to 10%, optionally from 0.01% to 10%. If more than one active metal is combined, they together generally can range from 0.001% up to 60% by weight of the catalyst. The molybdenum, indium, phosphorous, zinc or combinations thereof can, at least partially be present in the metallic, or zero valent, phase. The molybdenum, indium, phosphorous, zinc or combinations thereof can form alloys with the nickel and be present in the metallic phase.

The supports of the present disclosure can be any suitable support, such as for non-limiting examples: silicon dioxide, aluminum oxide, titanium dioxide, silica pillared clays, metal modified silica, metal oxide modified silica, silica-pillared clays, metal oxide modified silica-pillared clays, silica-pillared micas, metal oxide modified silica-pillared micas, silica-pillared tetrasilicic mica, silica-pillared taeniolite, and combinations thereof. Such supports are commercially obtainable or prepared by techniques known to those skilled in the art.

Prior art also describes the use of metal-containing zeolite catalysts, in which the metal is incorporated into the zeolite structure by some process, such as ion exchange or impregnation. However, swings in catalytic activity may occur in the case of a metal impregnated catalyst as metal can be lost from the pore structure of a zeolite or molecular sieve type substrate. Another drawback is the high probability of plugging of pores with coke when the metal is incorporated into a zeolite or molecular sieve type structure.

In one embodiment, the catalyst can be prepared by combining a substrate with the active metal elements. Embodiments of a substrate can be a molecular sieve, from either natural or synthetic sources. Zeolites can be an effective substrate, can be commercially available, and are well known in the art. Alternate molecular sieves also contemplated are zeolite-like materials such as crystalline silicoaluminophosphates (SAPO) and the aluminophosphates (ALPO).

The present disclosure is not limited by the method of catalyst preparation, and all suitable methods should be considered to fall within the scope herein. Conventional methods include co-precipitation from an aqueous, an organic, or a combination solution-dispersion, impregnation, dry mixing, wet mixing or the like, alone or in various combinations. In general, any method can be used which provides compositions of matter containing the prescribed components in effective amounts. According to an embodiment the substrate is charged with active metal via an incipient wetness impregnation. Other impregnation techniques such as by soaking, pore volume impregnation, or percolation can optionally be used. Alternate methods such as ion exchange, wash coat, precipitation, and gel formation can also be used.

When slurries, precipitates or the like are prepared, they will generally be dried, usually at a temperature sufficient to volatilize the water or other carrier, such as from 100° C. to 250° C., with or without vacuum. Irrespective of how the components are combined and irrespective of the source of the components, the dried composition can be calcined in the presence of a free oxygen-containing gas, usually at temperatures between about 300° C. and about 800° C. for from 30 min to 24 hours. The calcination can be in an oxygen-containing atmosphere, or alternately in a reducing or inert atmosphere.

Binder material, extrusion aids or other additives can be added to the catalyst composition or the final catalyst composition can be added to a structured material that provides a support structure. For example, the catalyst component and/or the composite catalyst can include an alumina or aluminate framework as a support. Upon calcination these elements can be altered, such as through oxidation which would increase the relative content of oxygen within the final catalyst structure. The combination of the composite catalyst of the present invention combined with additional elements such as a binder, extrusion aid, structured material, or other additives, and their respective calcination products, are included within the scope of the invention.

The prepared catalyst can be ground, pressed, sieved, shaped and/or otherwise processed into a form suitable for loading into a reactor. The reactor can be any type known in the art, such as a fixed bed, fluidized bed, or swing bed reactor. Optionally an inert material, such as quartz chips, can be used to support the catalyst bed and to locate the catalyst within the bed. Depending on the catalyst, a pretreatment of the catalyst may, or may not, be necessary. For the pretreatment, the reactor can be heated to elevated temperatures, such as 200° C. to 800° C. with an air flow, such as 100 mL/min, and held at these conditions for a length of time, such as 1 to 3 hours. Then, the reactor can be brought to the operating temperature of the reactor, for example 450° C. to 750° C., or optionally down to atmospheric or other desired temperature. The reactor can be kept under an inert purge, such as under a nitrogen or helium purge.

The catalyst of the present disclosure can be contacted with a feedstream containing $C_2$ to $C_5+$ alkanes under dehydrogenation conditions, for a time and at a temperature and pressure sufficient to produce olefins. It is desirable that mono-olefins will be produced. The alkanes may be co-fed with a stream of $H_2$ and/or inert gas. The $H_2$:alkane or inert:alkane ratio can range from about 0 to 5, optionally 0.1 to 2.0. Steam may also be co-fed if desired as a diluent or as a heat transfer agent.

In an embodiment the catalyst of the present disclosure can undergo in-situ regeneration, which can lower operating costs by decreasing the amount of time the reactor must be offline. The regeneration can be done by hydrogen and water vapor stripping at the reaction temperature. In an embodiment the catalyst of the present disclosure can undergo ex-situ regeneration.

In another embodiment, the disclosure is a process for the dehydrogenation of alkanes to olefins. The process includes the steps of introducing an alkane feedstock into a reaction chamber, passing the feedstock over a dehydrogenation catalyst at reaction conditions effective to provide a product containing olefin hydrocarbons, and regenerating the catalyst in-situ, when necessary.

The alkane feedstock can be alkanes containing less than 10 carbon atoms. The feedstock can consist primarily of $C_2$-$C_6$ alkanes. An embodiment of the invention provides for the use of ethane or propane or butane or a mixture of these gases as the starting material. Embodiments of the invention are particularly suitable for the production of ethene or propene or butenes or a mixture of these olefins. The alkane feedstock can be obtained from the side product of various hydrocarbon processing plants, for instance, the offgas of an FCC cracker or other refinery units, refinery fuel gas and shale gas hydrocarbons. One source of alkane feedstock is from natural gas liquids (NGL's) that can be extracted by gas processing plants, often a cryogenic process that extract the NGL's from a gas stream, such as a gas stream produced from a shale formation. One source of alkane feedstock is liquid petroleum gas (LPG), which consists mainly of the propane and butane fraction and can be recovered from gas and oil fields and petroleum refining operations. Co-feed can contain hydrogen. In an illustrative embodiment the alkane feed can contain primarily ethane. In an illustrative embodiment the alkane feed can contain primarily propane. In an illustrative embodiment the alkane feed can contain primarily butane. In an illustrative embodiment the alkane feed can contain primarily ethane and propane. In an illustrative embodiment the alkane feed can contain primarily propane and butane. In an illustrative embodiment the alkane feed can contain primarily butane and pentane. In an illustrative embodiment the alkane feed can contain primarily $C_3$-$C_6$ alkanes. In an illustrative embodiment the alkane feed can contain primarily $C_2$-$C_6$ alkanes.

The reaction chamber can house any suitable catalyst system, such as a fixed catalyst bed, a moving bed or a fluidized bed. Single or multiple catalyst beds can be used, and the reactor can be a swing reactor. The catalysts described herein may be used in any suitable reactor. The process could utilize a series of fixed bed reactors, where each reactor could be independently regenerated, a moving bed reactor where the catalysts moves through the reactor and is regenerated in a separate section of the plant, or a fluidized bed reactor, where the catalyst is circulated through the reactor and regenerated in a separate vessel.

The reaction can take place at a temperature of from 350° C. to 1000° C., optionally from 400° C. to 800° C., optionally from 450° C. to 750° C. For example, the reaction may take place at up to 400° C., 450° C., 500° C., 550° C., 600° C., 650° C., 700° C., 750° C., 800° C., 850° C., 900° C., 950° C., or 1000° C. The pressure can be in the range of from 3 psig to 600 psig, optionally from 3 psig to 300 psig, optionally from 3 psig to 150 psig. The weight hourly space velocity can be from 0.3 to 20 $hr^{-1}$, optionally from 0.3 to 10 $hr^{-1}$, and optionally from 0.3 to 3 $hr^{-1}$.

The dehydrogenation reaction can be performed adiabatically or non-adiabatically or approximately isothermally. If the dehydrogenation is performed in an adiabatically operated catalyst bed, the endothermic reaction will cause the temperature to decrease over the length of the catalyst bed. The reaction rate in the catalyst bed is thus limited so that several catalyst beds are typically required to achieve the desired high reaction rates and re-heating is necessary downstream of each catalyst bed. In order to achieve reasonable reaction rates, several catalyst beds are normally arranged in series and the reaction system is re-heated downstream of each catalyst bed.

If the dehydrogenation is performed in a non-adiabatically operated catalyst bed, the catalyst bed can be heated in order to maintain a high temperature. Because of the fact that the temperature in the reaction system is kept constant, the reaction rates may be kept appropriately high. Because of the location of the point of thermodynamic equilibrium, however, the disadvantage is that these high reaction rates can only be achieved at high temperatures, as a result of which the selectivity of olefin formation may be reduced. Hence, consecutive reactions will increasingly take place, so that undesired products may form, such as $CH_4$, $C_2H_4$, $C_2H_6$ and coke.

The by-products thus formed, especially finely dispersed coke, can precipitate in the course of the reaction on the catalyst, thus causing its state to change continually. The catalyst becomes coated with an undesired substance and is thus less accessible for the reactants. This means that the catalyst becomes deactivated. The activity of the catalyst for alkane dehydrogenation and the selectivity for alkene formation may in turn deteriorate. This would result in deterioration of the efficiency of the process as a whole. Because of operational requirements, such a deactivation can only be tolerated up to certain limit, because an economically viable operation of the plant could no longer be guaranteed. In order to counter-act this negative influence on the process, the catalyst will have to be regenerated after a certain reaction period in order to recover its activity.

Depending on its characteristics, the catalyst can be regenerated by bringing it in contact with an oxygen-bearing gas under conditions defined for the regeneration of the catalyst. The conditions for such a regeneration may differ from those required for the dehydrogenation. An oxygen-bearing gas diluted with steam may also be fed through the catalyst. As a result of this procedure, the by-products on the catalyst are reduced, with the result that the catalyst can regain its activity. If an oxygen-bearing gas diluted with steam is used for catalyst regeneration, the carbon-bearing deposit reacts to form carbon dioxide as the main product. The carbon-bearing deposit is converted to gaseous products by this reaction and is removed from the system.

As the conditions for the alkane dehydrogenation process differ from the catalyst regeneration process, the alkane dehydrogenation process will be interrupted after a certain period of operation and substituted by the catalyst regeneration process. Thereafter, the reactor bed is purged and again made available for dehydrogenation. Both these processes, i.e. the alkane dehydrogenation and catalyst regeneration, are thus performed periodically. In order to render the overall process economically efficient, this can take place in two or a plurality of catalyst beds, in which the reaction and regeneration processes are alternately implemented. In order to ensure optimum catalyst regeneration, regeneration process should be instrumented and monitored.

The reaction products can be processed and separated by cooling or other standard recovery or separation techniques.

The following examples are given to provide a better understanding of the present invention and are not intended to limit the scope of the invention in any way.

Experimental Data

Comparative Ni/C Catalyst Preparation

A comparative monometallic Ni/C (Ni loading 3 wt %) catalyst was synthesized using the impregnation method using $Ni(NO_3)_2 \cdot 6H_2O$ as a precursor. An amount of 0.2996 g of $Ni(NO_3)_2 \cdot 6H_2O$ was dissolved in 2.0 mL of DI $H_2O$ and 1.0 mL of concentrated $NH_4OH$ was added to adjust the pH obtaining a clear blue solution. Multi-wall carbon nanotube (10-20 nm outer diameter, Cheap tubes, Inc.) material was used as the support and was dried in air at 125° C. prior to use. An amount of 2.0 g of the dry carbon nanotube was impregnated with the Ni solution and then dried at 125° C. in air overnight (for approximately 16 hours), before reduction with 5% $H_2/N_2$ at 550° C. (ramp rate: 5° C./min, and held at 550° C. for 30 mins). Catalyst Ni/C contained nickel loading of 3 wt %.

A second comparison $Ni/SiO_2$ catalyst (Ni loading 2.7 wt %) was synthesized using strong electrostatic adsorption. 15.0 g of $Ni(NO_3)_2 \cdot 6H_2O$ was dissolved in 100 mL of deionized water followed by addition of 25.0 mL of concentrated $NH_4OH$. A clear blue solution was obtained with pH of 11. 50.0 g of $SiO_2$ (Davisil Grade 636, pore size 60 Å, 35-60 mesh, surface area 480 $m^2/g$) was added to the solution and the obtained suspension was stirred at room temperature for 20 mins. An additional 5.0 mL of $NH_4OH$ was added to maintain the pH at 11 at the end of the reaction. It was stirred at room temperature for additional 10 mins before filtration and thorough washing with DI water. The obtained Ni-adsorbed $SiO_2$ was dried at 125° C. overnight (for approximately 16 hours), and calcined at 300° C. for 30 mins (5° C. ramp to 300° C.). The Ni loading was determined by atomic adsorption spectroscopy (AAS) to be 2.7 wt %.

Bimetallic Ni—In/$SiO_2$ Catalyst Preparation

Bimetallic Ni—In/$SiO_2$ catalyst was synthesized by sequential incipient wetness impregnation (s-IWI) under controlled pH conditions using $Ni(NO_3)_2$ and $In(NO_3)_3$ salts as the precursors. Davisil Grade 636 $SiO_2$ (pore size 60 Å, 35-60 mesh) was dried at 125° C. in air overnight (for approximately 16 hours), prior to use. An amount of 0.3062 g of $Ni(NO_3)_2 \cdot 6H_2O$ was dissolved in 2.5 mL of DI $H_2O$, and about 2 mL of concentrated $NH_4OH$ was added to adjust the pH to 11. An amount of 3.0 g of dry $SiO_2$ was impregnated with the Ni solution followed by drying at 125° C. in air overnight (for approximately 16 hours). The sample was impregnated with 2.0 mL $In(NO_3)_3$ solution which contains 0.9418 g of $In(NO_3)_3 \cdot xH_2O$. The sample was then calcined in air at 300° C. A ramp rate of 2° C./min was used up to 300° C. and then held at 300° C. for 3 hours. The catalyst was reduced with $H_2$ at 600° C. for 30 mins (ramp rate: 5° C./min) before the dehydrogenation test. Catalyst Ni—In/$SiO_2$ contained nickel loading of 2 wt % and indium loading of 11 wt %.

Bimetallic Ni—Mo/C Catalyst Preparation

Bimetallic Ni—Mo/C catalyst was synthesized using a co-impregnation method using $Ni(NO_3)_2 \cdot 6H_2O$ and $Na_2MoO_4$ as the precursors. An amount of 0.2996 g of $Ni(NO_3)_2 \cdot 6H_2O$ and 0.2114 g of $Na_2MoO_4$ were dissolved in 2.0 mL of DI $H_2O$ and 1.0 mL of concentrated $NH_4OH$ was added to adjust the pH obtaining a clear blue solution. Multi-wall carbon nanotube (10-20 nm outer diameter, Cheap tubes, Inc.) material was used as the support and was dried in air at 125° C. prior to use. An amount of 2.0 g of the dry carbon nanotube was impregnated with the Ni—Mo solution and then dried at 125° C. in air overnight before reduction with 5% $H_2/N_2$ at 550° C. (ramp rate: 5° C./min, and held at 550° C. for 30 mins). Catalyst Ni—Mo/C contained nickel loading of 3 wt % and molybdenum loading of 5 wt %.

Catalyst Testing

Propane Dehydrogenation

Propane dehydrogenation kinetics measurements were carried out in a vertical quartz tube fixed-bed reactor with ⅜-inch ID equipped with gas flow meters and gas chromatography (GC) for product analysis. The weight of the catalyst used was 1.0 g supported on quartz wool within the quartz tube. A thermocouple within a stainless-steel thermocouple well was placed at the bottom center of the catalyst bed to measure the reaction temperature inside the bed. The products were analyzed with an Agilent gas chromatograph system equipped with a Flame Ionization Detector (FID).

Initially, the catalyst was flushed with Ar at 50 mL/min at room temperature to flush out all the air, and then the temperature of the reactor was raised to the reaction temperature (i.e., 550° C. or 600° C.) with 50 mL/min 5% $H_2/N_2$ flow and held for 30 minutes for stabilization. The propane feed is 5.0% balanced with $N_2$, and co-feeding $H_2$ or $N_2$ is applied to maintain constant space velocity for comparison. The pressure was maintained at 1.0 atm. Product concentrations were analyzed by a flame ionization detector (FID) using $H_2$ and air.

Figure 1:
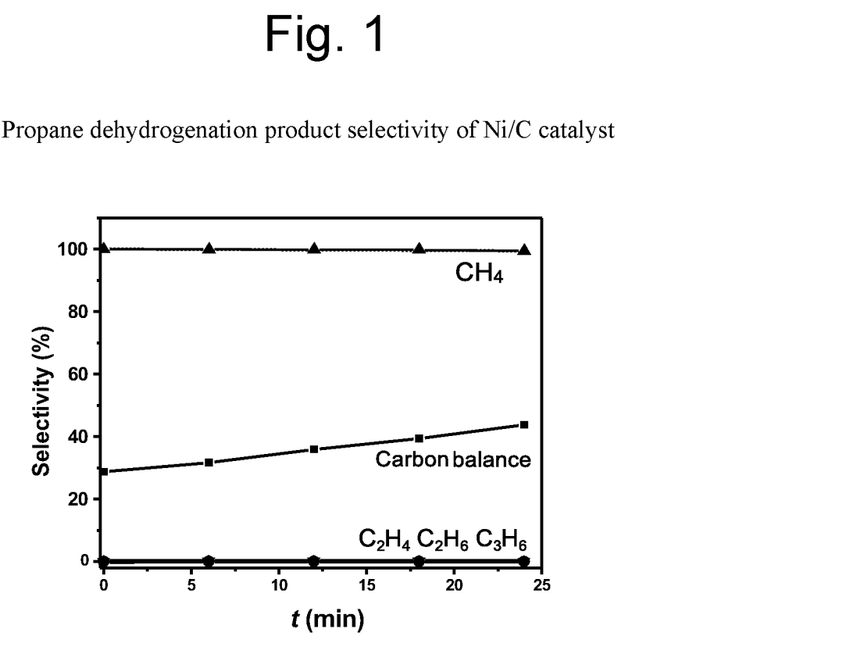
FIG. 1 is a graph of the selectivity of Ni/C catalyst in propane dehydrogenation.
Figure 2:
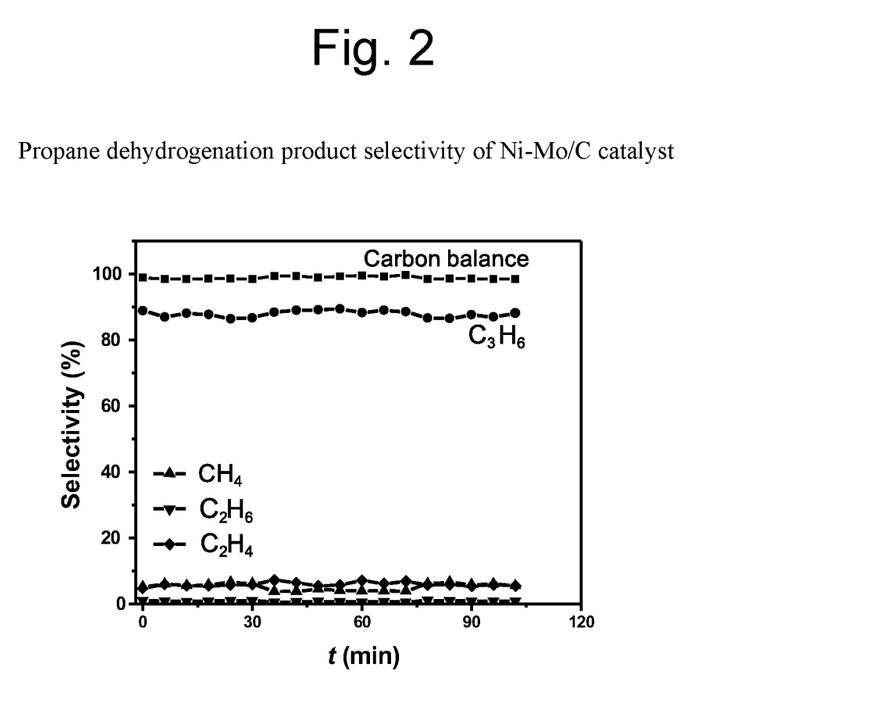
FIG. 2 is a graph of the selectivity of Ni—Mo/C catalyst in propane dehydrogenation.

The results for the Ni/C and Ni—Mo/C catalysts in propane dehydrogenation are shown in FIGS. 1 and 2 and Table 1. The propane dehydrogenation testing of both Ni/C (Ni loading 3 wt %) and Ni—Mo/C (Ni loading 3 wt %) catalysts were conducted at 550° C. under the same space velocity. The Ni/C catalyst shows a low carbon balance of 30-40%, while bimetallic catalyst Ni—Mo/C shows very high carbon balance approaching 100% suggesting that the Ni—Mo/C catalyst has very slow coke deposition. In the gas phase products, Ni/C shows almost 100% selectivity to $CH_4$, and only a trace amount of $C_3H_6$ was observed. However, the Ni—Mo/C catalyst shows 88% selectivity to $C_3H_6$, and only 5% to $CH_4$. The addition of Mo forming a bimetallic Ni—Mo catalyst greatly minimizes the coke deposition and improves the $C_3H_6$ selectivity.

TABLE 1

Comparison of the propane dehydrogenation results on Ni/C and Ni—Mo/C

| Catalyst | Carbon balance (%) | Selected gas phase product selectivity (%) | |
|---|---|---|---|
| | | $C_3H_6$ | $CH_4$ |
| Ni/C | 30-40 | 0 | 100 |
| Ni—Mo/C | 98 | 88 | 5 |

Figure 3:
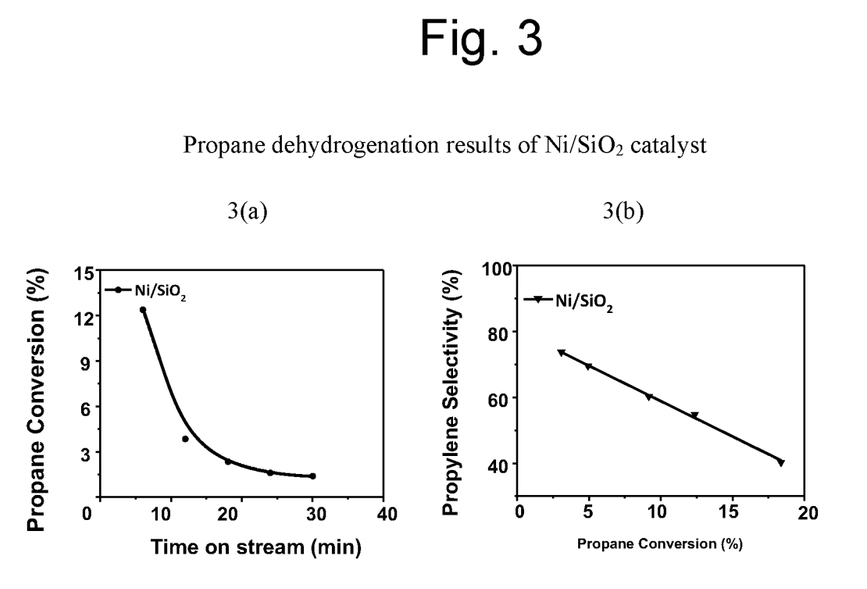
FIGS. 3a and 3b are graphs of the conversion of propane dehydrogenation as a function of time on stream and propylene selectivity as a function of conversion, respectively.

Reaction conditions: 550° C., 1.0 atm., 0.5 g of the catalyst, 50 mL/min 5% $C_3H_8/N_2$ The $C_3H_8$ dehydrogenation catalytic performance testing of $Ni/SiO_2$ was conducted at 600° C. in a vertical, ½" OD quartz tube reactor equipped with mass flow controllers. The catalyst was supported on quartz wool with an internal thermocouple monitoring the temperature of the catalyst bed. Initially, the catalyst was purged with ultra-high purity $N_2$ at 50 mL/min at room temperature and ramped to 600° C. at 10° C./min. The stability test of $Ni/SiO_2$ was done using 0.1 g of the catalyst with 100 mL/min of 5.0% $C_3H_8/N_2$ flow plus 50 mL/min 5.0% $H_2/N_2$ flow, at 1.0 atm. Other tests on $Ni/SiO_2$ was done using 100 mL/min of 5.0% $C_3H_8/N_2$ flow plus 50 mL/min 5.0% $H_2/N_2$ flow with various amounts of the catalyst to achieve a range of the conversion between 2-20%, and the initial data point was used for the selectivity-conversion plots. The results for $Ni/SiO_2$ are shown in FIGS. 3a and 3b.

Figure 4:
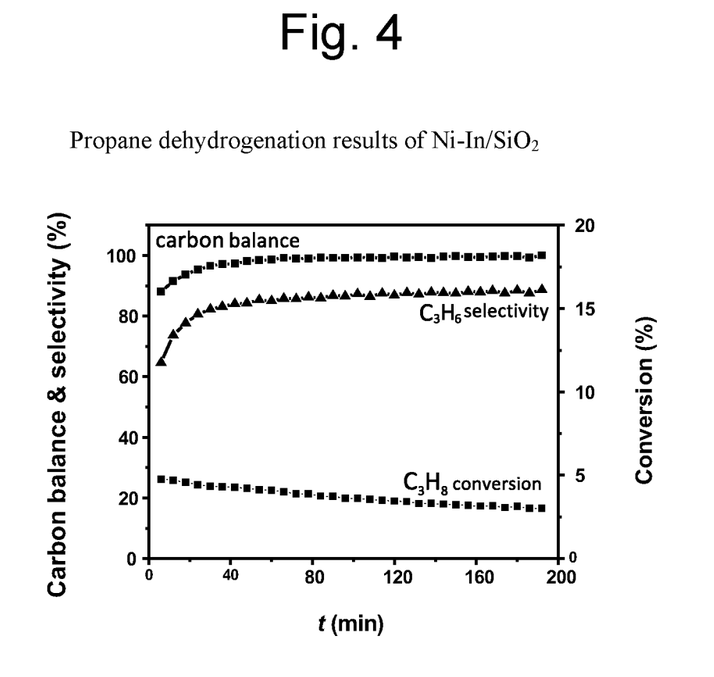
FIG. 4 is a graph of the conversion, selectivity and carbon balance of Ni—In/$SiO_2$ catalyst in propane dehydrogenation.

The results for the Ni—$In/SiO_2$ catalyst in propane dehydrogenation are shown in FIG. 4 and Table 2. The Ni—$In/SiO_2$ catalyst shows good selectivity toward propylene and high carbon balance (low coke deposition). As shown in FIG. 4, the carbon balance started out at about 90% and reaches almost 100% after about 1 hour on stream. Propylene selectivity started with 65% and reached 85% after 1 hour on stream. The catalyst deactivates at a reasonably slow rate, and in the first three hours of the test, the conversion dropped from 4.5% to 3.0%, which corresponds roughly to a 30% drop of the rate. It was found that alloying Ni with main group metals can lead to high selectivity dehydrogenation catalysts.

TABLE 2

Propane dehydrogenation results on Ni—In/SiO2

| Catalyst | Carbon balance (%) | $C_3H_6$ selectivity (%) |
|---|---|---|
| Ni/SiO2 | 40-50% | 40-75 |
| Ni—In/SiO2 | 90-100 | 65-85 |

Catalyst Structure Analysis

Figure 5:
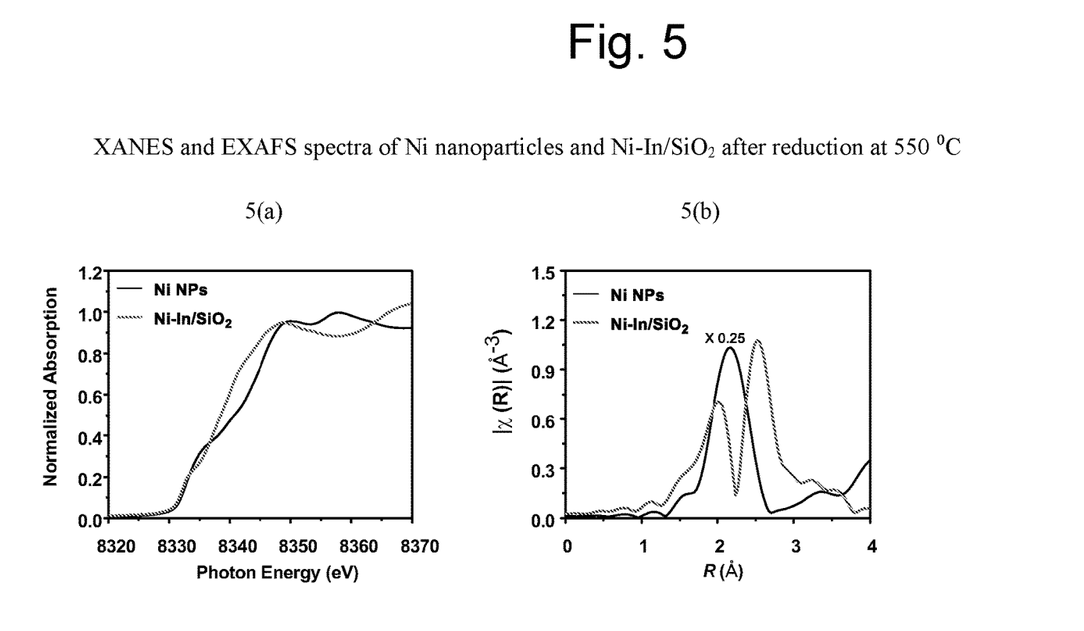
FIG. 5 are graphs of the XANES and EXAFS spectra of Ni nanoparticles and Ni—In/$SiO_2$ catalyst after reduction at 550° C.
Figure 6:
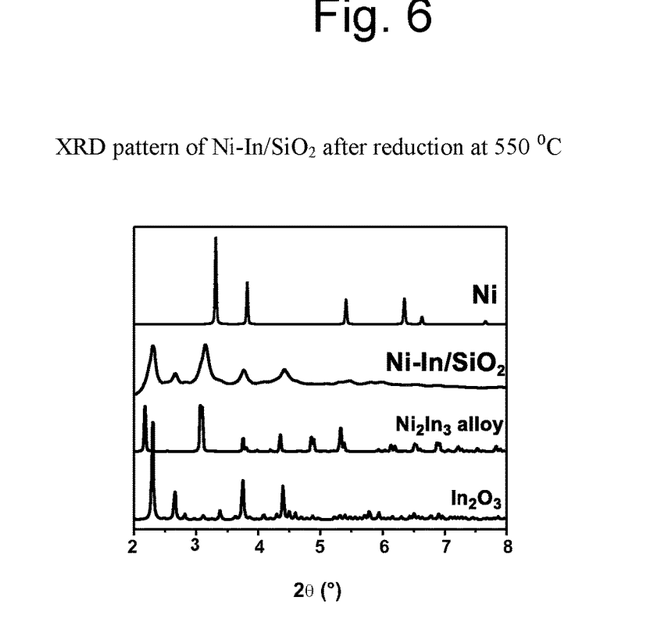
FIG. 6 is a graph of the XRD pattern of Ni, Ni—In/$SiO_2$ catalyst, $Ni_2In_3$ alloy, and $In_2O_3$.

Comparison of the XANES spectrum of the Ni—$In/SiO_2$ catalyst with nickel nanoparticles (Ni NPs), as shown in FIG. 5, suggest that the oxidation state of Ni is Ni(0) in the Ni—$In/SiO_2$ catalyst. The EXAFS spectrum, as shown in FIG. 5, shows the In neighbors surrounding Ni suggesting the formation of a Ni—In alloy. The XRD results, shown in FIG. 6, suggest the presence of $Ni_2In_3$ alloy as well as $In_2O_3$. No Ni(0) nanoparticles were observed in the XRD pattern. These results suggest that the $Ni_2In_3$ alloy is active for propane dehydrogenation with high selectivity toward propylene, as well as low coke deposition and high catalyst stability.

Ni-Based Bimetallic Catalysts that do not Form Alloy or do not Lead to Selective Dehydrogenation Catalysts It has been found that Ni—$Ga/SiO_2$ forms alloy $Ni_3Ga$, but it is not selective toward propylene. It has been found that Ni—$Sb/SiO_2$ does not form ally and does not work for propane dehydrogenation. It has further been found that Ni—$Bi/SiO_2$ does form an alloy, but it is not active for propane dehydrogenation. Synthesis and characterization of these materials are shown here.

A Ni—$Ga/SiO_2$ catalyst was synthesized using a sequential impregnation process. Davisil Grade 636 $SiO_2$ (pore size 60 Å, 35-60 mesh) was dried at 125° C. in air overnight prior to use. An amount of 0.2901 g of $Ni(NO_3)_2 \cdot 6H_2O$ was dissolved in 2.5 mL of DI $H_2O$, and concentrated $NH_4OH$ was added to adjust the pH to 10. The solution was then impregnated onto 3.0 g of dry $SiO_2$. After being dried in air at 125° C. in air, the sample was impregnated with 2.0 mL of $Ga(NO_3)_3$ solution containing 0.5314 g of $Ga(NO_3)_3 \cdot xH_2O$. After being dried in air, the catalyst was calcined in air at 300° C. for 3 hours (ramp rate 2° C./min). The catalyst was reduced with 5% $H_2/N_2$ at 650° C. prior the dehydrogenation test.

A Ni—$Sb/SiO_2$ catalyst was also synthesized using sequential impregnation. An amount of 0.7650 g of $SbCl_3$ was dissolved in 10 mL of acetone, and was then impregnated onto 10.0 g of the dry $SiO_2$. The sample was calcined in air at 300° C. for 3 hours (ramp rate 2° C./min), and $Sb/SiO_2$ was obtained. An amount of 0.20 g of $Ni(NO_3)_2 \cdot 6H_2O$ was dissolved in 2 mL of DI $H_2O$, and concentrated $NH_4OH$ was added to adjust the pH to 10. The obtained blue solution was impregnated onto 4.0 g of the $Sb/SiO_2$ which was subsequently calcined at 300° C. for 3 hours (ramp rate 2° C./min).

A Ni—$Bi/SiO_2$ catalyst was also synthesized using sequential impregnation. An amount of 1.6458 g of $Bi(NO_3)_3 \cdot 5H_2O$ was mixed with 5 mL of DI $H_2O$, and 3 mL of concentrated $HNO_3$ was added to get a clear solution which was then impregnated onto 10.0 g of the dry $SiO_2$. The sample was calcined in air at 300° C. for 3 hours (ramp rate 2° C./min), and $Bi/SiO_2$ was obtained. An amount of 0.20 g of $Ni(NO_3)_2 \cdot 6H_2O$ was dissolved in 2 mL of DI $H_2O$, and concentrated $NH_4OH$ was added to adjust the pH to 10. The obtained blue solution was impregnated onto 4.0 g of the $Bi/SiO_2$ which was subsequently calcined at 300° C. for 3 hours (ramp rate 2° C./min).

TABLE 3

EXAFS fitting results of the Ni—$Ga/SiO_2$ catalyst

| C.N. | amp | $E_0$ (eV) | R(Å) | sigma$^2$ |
|---|---|---|---|---|
| 8 X Ni—Ni | 0.742 ± 0.047 | 5.6 ± 1.4 | 2.53 ± 0.02 | 0.008 ± 0.005 |
| 4 X Ni—Ga | | | | 0.009 ± 0.013 |

Figure 7:
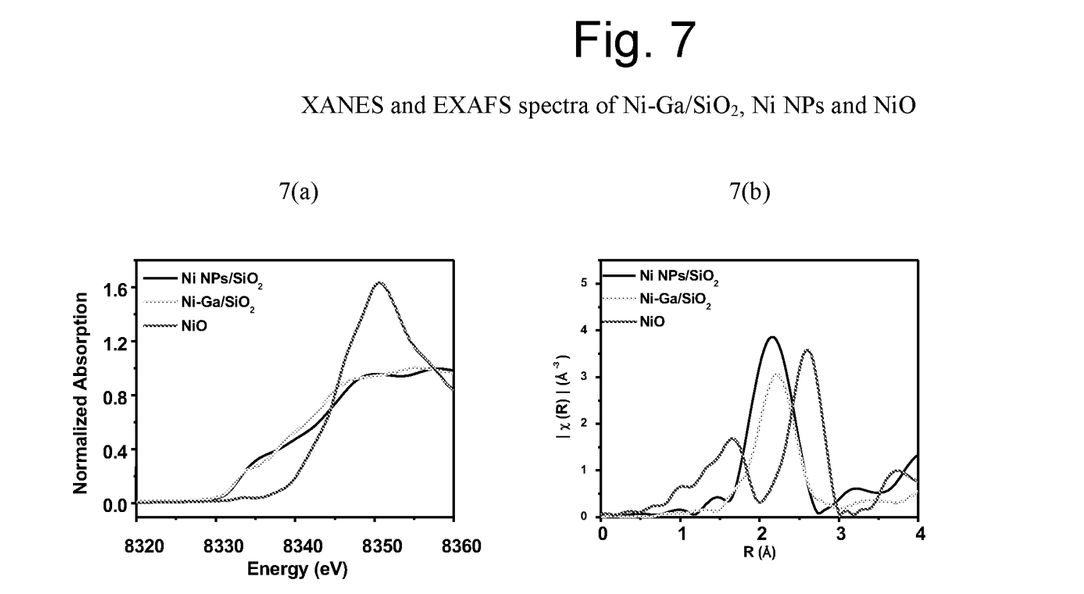
FIG. 7 are graphs of XANES and EXAFS spectra of Ni nanoparticles, Ni—Ga/$SiO_2$ catalyst and NiO.
Figure 8:
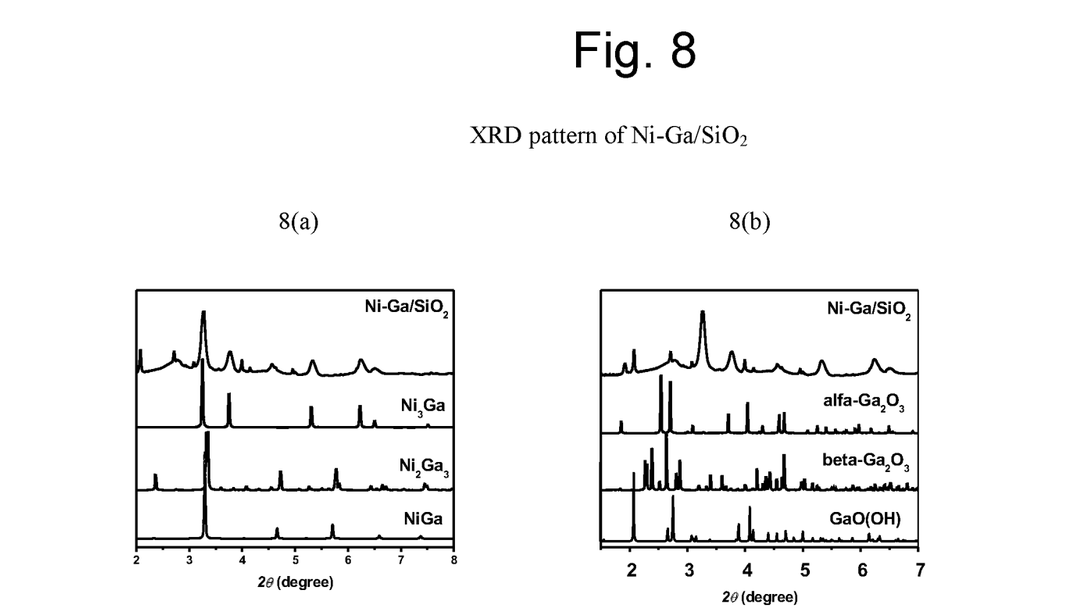
FIG. 8 are graphs of the XRD pattern of Ni—Ga/$SiO_2$ catalyst, $Ni_3Ga$ alloy, $Ni_2Ga_3$ alloy, NiGa alloy, alfa-$Ga_2O_3$, beta-$Ga_2O_3$, and GaO(OH).

FIG. 7 compares the XANES and EXAFS spectra of Ni—$Ga/SiO_2$ with Ni NPs and NiO. The XANES spectra confirm the oxidation state of Ni is Ni(0), and the EXAFS spectra suggest the absence of oxygen neighboring atoms. The fitting results of the EXAFS data are summarized in Table 3, which agrees well with the formation of $Ni_3Ga$ alloy phase. The XRD scattering pattern excluded the possibility of other Ni$_x$Ga$_y$ alloy phases including Ni$_2$Ga$_3$ and NiGa phases. The presence of various gallium oxides and hydroxides was also confirmed by the XRD pattern as shown in FIG. 8.

Figure 9:
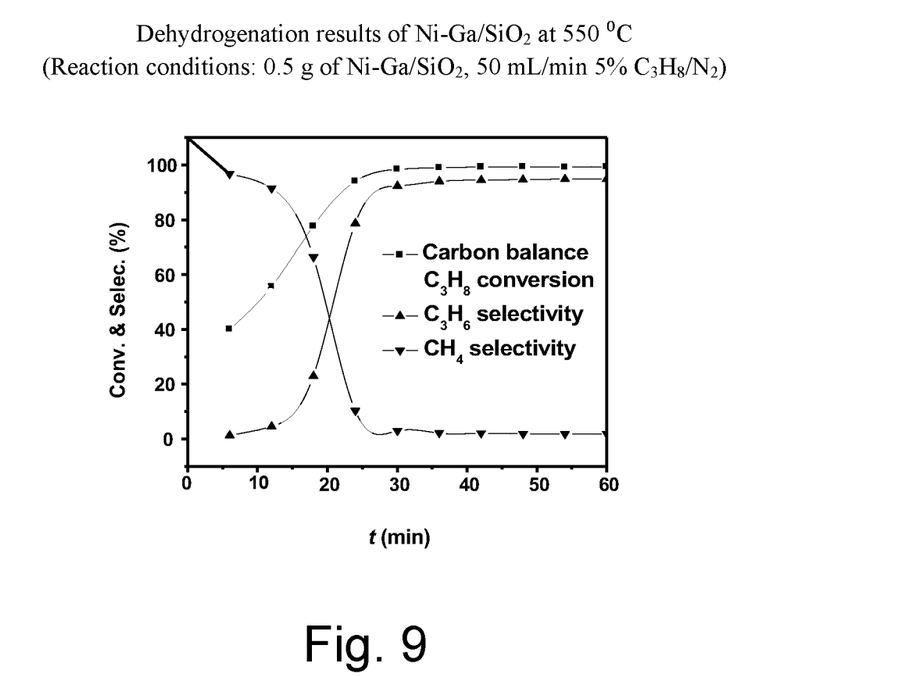
FIG. 9 is a graph of propane dehydrogenation results of the Ni—Ga/$SiO_2$ catalyst.

The C$_3$H$_8$ dehydrogenation results are shown in FIG. 9. The reaction conditions were: 0.5 g of Ni—Ga/SiO$_2$, flow rate of 50 mL/min of 5% C$_3$H$_8$/N$_2$. Starting with very high propane conversion of about 80% and very low propylene selectivity, the Ni$_3$Ga alloy deactivates very fast in the first 30 minutes of the test. The conversion dropped to about 5% with about 90% propylene selectivity. Compared with Ni NPs shown in FIG. 1, the Ni—Ga/SiO$_2$ catalyst shows much better selectivity at lower conversion, but still not good enough for a practical application.

Figure 10:
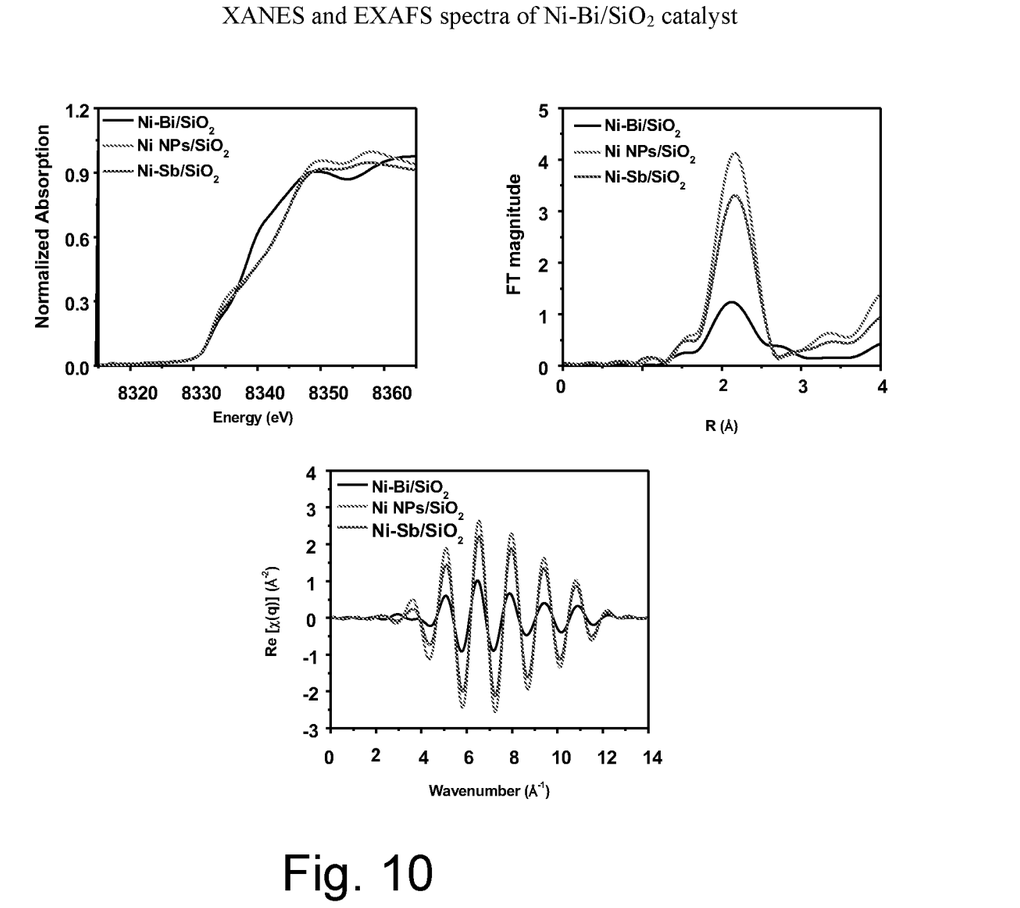
FIG. 10 are graphs of the XANES and EXAFS spectra of the Ni—Bi/$SiO_2$ catalyst.

As shown in FIG. 10, the oxidation state of Ni(0) was confirmed in both Ni—Sb/SiO$_2$ and Ni—Bi/SiO$_2$. In the R-space EXAFS spectra, both catalysts show a smaller magnitude than Ni NPs; while in the q-space data, Ni—Sb/SiO$_2$ share the nodes with Ni NPs suggesting that the Ni—Sb/SiO$_2$ is mostly Ni(0) probably with a surface layer of Sb. The Ni—Bi/SiO$_2$ q-space data shows smaller magnitude, as well as a shift of the nodes suggesting the presence of Bi neighbors. The EXAFS fittings results as shown in Table 4, using Ni+NiBi alloy as the model suggest the formation of NiBi alloy shell on the surface with a Ni core.

TABLE 4

EXAFS fitting results of the Ni—Bi/SiO$_2$ catalyst

|  | N * S$_0^2$ | R | ΔE$_0$ | σ$^2$ | Crystal Structure |
|---|---|---|---|---|---|
| Ni—Bi | 6 * 0.287 | 2.68 | 1.6 | 0.008 | NiBi alloy: 6 * Ni—Bi@2.70 |
| Ni—Ni | 12 * 0.310 | 2.48 | 3.6 | 0.008 | Ni: 12 * Ni—Ni@2.49 |

Figure 11:
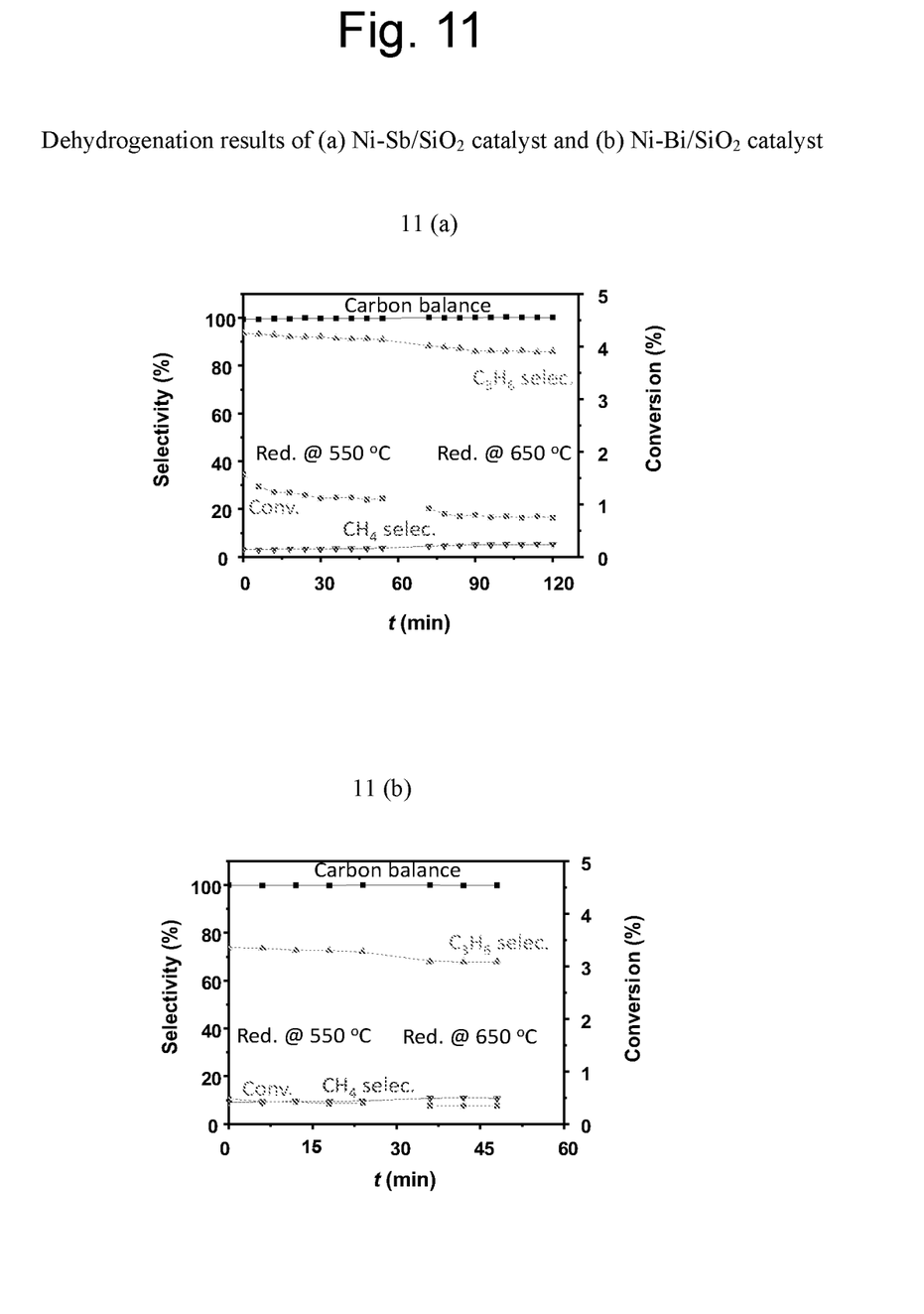
FIG. 11 are graphs of the dehydrogenation results of the Ni—Sb/$SiO_2$ and Ni—Bi/$SiO_2$ catalysts.

Both Ni—Sb/SiO$_2$ and Ni—Bi/SiO$_2$ are not very active for propane dehydrogenation at 550° C., as shown in FIG. 11. The Reaction conditions are: 0.7 g of Ni—Sb/SiO$_2$ or Ni—Bi/SiO$_2$, flow rate of 50 mL/min of 5% C$_3$H$_8$/N$_2$. The Ni—Sb/SiO$_2$ catalyst gives about 1% conversion; while the Ni—Bi/SiO$_2$ catalyst gives 0.5% conversion, neither of which is very active. A further reduction at 650° C. did not improve the catalysis compared with the results from the reduction at 550° C.

Summary of Results:

Ni alloys with main group metals (Ni—In as an example) are active and selective for alkane dehydrogenation Ni alloys with transition metals (Ni—Mo as an example) are active and selective for alkane dehydrogenation Fe and Co for similar alloy structures and would be expected to be effective alkane dehydrogenation catalysts An embodiment of the present disclosure is a bimetallic catalyst composition that includes a Group VIII noble metal selected from the group consisting of nickel, iron, cobalt, and combinations thereof, a metal selected from the group consisting of molybdenum, indium, phosphorous, zinc and combinations thereof, and a support. In an embodiment the Group VIII noble metal is nickel, which can be present in an amount ranging from 0.001 wt % to 30 wt % on an elemental basis of the catalyst composition. In an embodiment the molybdenum, indium, phosphorous, zinc, and combinations thereof, can be present in an amount from 0.001 wt % to 30 wt % on an elemental basis of the catalyst composition. In an embodiment the metal selected from the group consisting of molybdenum, indium, phosphorous, zinc, and combinations thereof are present, at least partially in the metallic phase. In an embodiment the support can be selected from the group consisting of silicon dioxide, aluminum oxide, titanium dioxide, zeolites, silica-alumina, cerium dioxide, zirconium dioxide, magnesium oxide, metal modified silica, silica-pillared clays, silica-pillared micas, metal oxide modified silica-pillared mica, silica-pillared tetrasilicic mica, silica-pillared taeniolite, zeolite, molecular sieve, and combinations thereof. In an embodiment the support is selected from the group consisting of silica, silicon dioxide, titanium dioxide, and metal modified silica. In an embodiment the Group VIII noble metal is selected from the group consisting of nickel, iron, cobalt, and combinations thereof and is present in an amount ranging from 0.001 wt % to 30 wt %, the molybdenum, indium, phosphorous, zinc, and combinations thereof is present in an amount from 0.001 to 30 wt %, and the support is selected from the group consisting of silicon dioxide, aluminum oxide, titanium dioxide, and metal modified silica. In an embodiment the catalyst is calcined and reduced. In an embodiment the catalyst is prepared using sequential incipient wetness impregnation. In an embodiment the catalyst is prepared using a co-impregnation method.

An embodiment of the present disclosure is a process for the dehydrogenation of alkanes to olefins that includes providing a catalyst with a Group VIII noble metal selected from the group consisting of nickel, iron, cobalt, and combinations thereof; a metal selected from the group consisting of molybdenum, indium, phosphorous, zinc, and combinations thereof, and a support. In an embodiment the metal selected from the group consisting of molybdenum, indium, phosphorous, zinc, and combinations thereof are present, at least partially in the metallic phase. The catalyst is contacted with a feedstream comprising C$_2$ to C$_5$+ alkanes under dehydrogenation conditions and a dehydrogenation reaction occurs converting a portion of the C$_2$ to C$_5$+ alkanes to C$_2$ to C$_5$+ olefins. In an embodiment the Group VIII noble metal is nickel. In an embodiment the Group VIII noble metal is present in an amount ranging from 0.001 wt % to 30 wt %. In an embodiment the molybdenum, indium, phosphorous, zinc, and combinations thereof, is present in an amount from 0.001 to 30 wt %. In an embodiment the method further includes regeneration of the catalyst when needed. In an embodiment the support is selected from the group consisting of silica, silicon dioxide, aluminum oxide, titanium dioxide, zeolites, silica-alumina, cerium dioxide, zirconium dioxide, magnesium oxide, metal modified silica, silica-pillared clays, silica-pillared micas, metal oxide modified silica-pillared mica, silica-pillared tetrasilicic mica, silica-pillared taeniolite, zeolite, molecular sieve, and combinations thereof. In an embodiment the feedstream further comprises hydrogen. In an embodiment the feedstream further comprises an inert gas. In an embodiment the feedstream further comprises steam. In an embodiment the feedstream comprises propane and selectivity to propylene is greater than 90%. In an embodiment the conversion of propane to olefins is at least 10%. In an embodiment the conversion of propane to olefins is at least 10% with selectivity to propylene of greater than 90% continues for at least 30 minutes, optionally at least 1 hour, optionally at least 2 hours, optionally at least 5 hours, optionally at least 10 hours, optionally at least 24 hours, optionally at least 48 hours, optionally at least 7 days, optionally at least 14 days, optionally at least 30 days. In an embodiment the feedstream comprises ethane and selectivity to ethylene is greater than 90%. In an embodiment the conversion of ethane to olefins is at least 30%. In an embodiment the conversion of ethane to olefins is at least 30% with selectivity to ethylene of greater than 90% continues for at least 30 minutes, optionally at least 1 hour, optionally at least 2 hours, optionally at least 5 hours, optionally at least 10 hours, optionally at least 24 hours, optionally at least 48 hours, optionally at least 7 days, optionally at least 14 days, optionally at least 30 days. In an embodiment the feedstream comprises $C_2$ to $C_5+$ alkanes and selectivity to $C_2$ to $C_5+$ olefins is greater than 90%. In an embodiment the conversion of $C_2$ to $C_5+$ alkanes to $C_2$ to $C_5+$ olefins is at least 10%. In an embodiment the conversion of propane to olefins is at least 10% with selectivity to propylene of greater than 90% continues for at least 30 minutes, optionally at least 1 hour, optionally at least 2 hours, optionally at least 5 hours, optionally at least 10 hours, optionally at least 24 hours, optionally at least 48 hours, optionally at least 7 days, optionally at least 14 days, optionally at least 30 days. In an embodiment the conversion of propane to olefins is at least 10% with selectivity to propylene of greater than 70% and the conversion of ethane to olefins is at least 10% with selectivity to ethylene of greater than 70%. In an embodiment the catalyst is regenerated in-situ when needed.

An embodiment of the present disclosure is a method of making a dehydrogenation catalyst that includes providing a support material, adding to the support material a Group VIII noble metal selected from the group consisting of nickel, iron, cobalt, and combinations thereof, and a metal selected from the group consisting of molybdenum, indium, phosphorous, zinc, and combinations thereof, to make a catalyst material, calcining the catalyst material; and reducing the catalyst material to form a dehydrogenation catalyst. In an embodiment the Group VIII noble metal is nickel. In an embodiment the Group VIII noble metal is present in an amount ranging from 0.001 wt % to 30 wt % on an elemental basis of the dehydrogenation catalyst composition. In an embodiment the metal selected from the group consisting of molybdenum, indium, phosphorous, zinc, and combinations thereof is present in an amount from 0.001 wt % to 30 wt % on an elemental basis of the dehydrogenation catalyst composition. In an embodiment the metal selected from the group consisting of molybdenum, indium, phosphorous, zinc, and combinations thereof are present, at least partially in the metallic phase. In an embodiment the support is selected from the group consisting of silica, silicon dioxide, aluminum oxide, titanium dioxide, zeolites, silica-alumina, cerium dioxide, zirconium dioxide, magnesium oxide, metal modified silica, silica-pillared clays, silica-pillared micas, metal oxide modified silica-pillared mica, silica-pillared tetrasilicic mica, silica-pillared taeniolite, zeolite, molecular sieve, and combinations thereof. In an embodiment the support is selected from the group consisting of silica, silicon dioxide, titanium dioxide, and metal modified silica. In an embodiment the metals are added using sequential incipient wetness impregnation. In an embodiment the metals are added using a co-impregnation method.

The text above describes one or more specific embodiments of a broader disclosure. The disclosure also can be carried out in a variety of alternate embodiments and thus is not limited to those described here. The foregoing description of an embodiment of the disclosure has been presented for to the purposes of illustration and description. It is not intended to be exhaustive or to limit the disclosure to the precise form disclosed. Many modifications and variations are possible in light of the above teaching. It is intended that the scope of the disclosure be limited not by this detailed description, but rather by the claims appended hereto.

What is claimed is:

1. A process for dehydrogenation of alkanes to olefins comprising:
    providing a supported metal alloy catalyst consisting of nickel and indium, and a support selected from the group consisting of silicon dioxide, aluminum oxide and combinations thereof; and
    contacting the supported metal alloy catalyst with a feedstream comprising one or more $C_2$ to $C_5+$ alkanes at reaction conditions sufficient to dehydrogenate a portion of the one or more $C_2$ to $C_5+$ alkanes to one or more $C_2$ to $C_5+$ olefins.

2. The process according to claim 1 wherein the nickel is present in an amount ranging from 0.001 wt % to 30 wt % on an elemental basis of the supported metal alloy catalyst.

3. The process according to claim 1 further comprising regeneration of the supported metal alloy catalyst.

4. The process according to claim 1 wherein the support is silicon dioxide.

5. The process according to claim 1 wherein the support is silicon dioxide; the nickel is present in an amount of 0.001 wt % to 30 wt % on an elemental basis of the supported metal alloy catalyst; and the indium is present in an amount of 0.001 wt % to 30 wt % on an elemental basis of the supported metal alloy catalyst.

6. The process according to claim 1 wherein the support is aluminum oxide.

7. A supported metal alloy catalyst composition comprising:
    a metal alloy consisting of nickel and indium; and
    a support,
    wherein the indium is present in an amount from 0.001 to 30 wt % on an elemental basis of the metal alloy and present, at least partially in a metallic phase and at least partially in an alloy phase.

8. The process according to claim 7 wherein nickel is present in an amount ranging from 0.001 wt % to 30 wt % on an elemental basis of the metal alloy catalyst.

9. The process according to claim 7 further comprising regeneration of the supported metal alloy catalyst.

10. The process according to claim 7 wherein the support is silicon dioxide, the nickel is present in an amount of 0.001 wt % to 30 wt % on an elemental basis of the supported metal alloy catalyst; and the indium is present in an amount of 0.001 wt % to 30 wt % on an elemental basis of the supported metal alloy catalyst.

11. The process according to claim 7 wherein the support is selected from the group consisting of silicon dioxide, aluminum oxide, titanium dioxide, zeolites, silica-alumina, cerium dioxide, zirconium dioxide, magnesium oxide, metal modified silica, silica-pillared clays, silica-pillared micas, metal oxide modified silica-pillared mica, silica-pillared tetrasilicic mica, silica-pillared taeniolite, molecular sieve, and combinations thereof.

12. The process according to claim 7 wherein the support is selected from the group consisting of silicon dioxide, aluminum oxide and combinations thereof.

* * * * *

UNITED STATES PATENT AND TRADEMARK OFFICE
CERTIFICATE OF CORRECTION

PATENT NO. : 12,059,670 B2
APPLICATION NO. : 16/635603
DATED : August 13, 2024
INVENTOR(S) : Jeffrey T. Miller and Guanghui Zhang Page 1 of 1

It is certified that error appears in the above-identified patent and that said Letters Patent is hereby corrected as shown below:

In the Claims

In Claim 8, Line 1: "The process according to claim 7" should be changed to "The catalyst composition according to claim 7."

In Claim 9, Line 1: "The process according to claim 7" should be changed to "The catalyst composition according to claim 7."

In Claim 10, Line 1: "The process according to claim 7" should be changed to "The catalyst composition according to claim 7."

In Claim 11, Line 1: "The process according to claim 7" should be changed to "The catalyst composition according to claim 7."

In Claim 12, Line 1: "The process according to claim 7" should be changed to "The catalyst composition according to claim 7."

Signed and Sealed this
Twenty-fourth Day of December, 2024

Derrick Brent
*Acting Director of the United States Patent and Trademark Office*